(12) United States Patent
Caruel et al.

(10) Patent No.: US 10,654,822 B2
(45) Date of Patent: May 19, 2020

(54) COMPOSITION AND RODENTICIDAL BAIT COMPRISING FLOCOUMAFEN, AND PROCESS FOR CONTROLLING TARGET RODENT PESTS

(71) Applicants: LIPHATECH, Pont-du-Casse (FR); INSTITUT ENSEIGNEMENT SUPERIEUR ET RECHERCHE EN ALIMENTATION SANTE ANIMALE SCIENCES AGRONOMIQUES ET ENVIRONNEMENT (VET AGRO SUP), Marcy l'Etoile (FR)

(72) Inventors: Hervé Caruel, Moncaut (FR); Etienne Benoit, Lyons (FR); Isabelle Fourel, Miribel (FR); Virginie Lattard, Lyons (FR)

(73) Assignees: LIPHATECH, Pont-du-Casse (FR); INSTITUT ENSEIGNEMENT SUPERIEUR ET RECHERCHE EN ALIMENTATION SANTE ANIMALE SCIENCES AGRONOMIQUES ET ENVIRONNEMENT (VET AGRO SUP), Marcy l'Etoile (FR)

( * ) Notice: Subject to any disclaimer, the term of this patent is extended or adjusted under 35 U.S.C. 154(b) by 0 days.

(21) Appl. No.: 16/061,115

(22) PCT Filed: Dec. 6, 2016

(86) PCT No.: PCT/EP2016/079865
§ 371 (c)(1),
(2) Date: Jun. 11, 2018

(87) PCT Pub. No.: WO2017/097753
PCT Pub. Date: Jun. 15, 2017

(65) Prior Publication Data
US 2018/0362489 A1    Dec. 20, 2018

(30) Foreign Application Priority Data
Dec. 11, 2015 (FR) ..................... 15 62169

(51) Int. Cl.
A01N 25/00 (2006.01)
C07D 311/56 (2006.01)
A01N 43/16 (2006.01)
B01D 15/38 (2006.01)

(52) U.S. Cl.
CPC .......... *C07D 311/56* (2013.01); *A01N 25/004* (2013.01); *A01N 43/16* (2013.01); *B01D 15/3833* (2013.01); *C07B 2200/07* (2013.01)

(58) Field of Classification Search
None
See application file for complete search history.

(56) References Cited

U.S. PATENT DOCUMENTS

| | | | |
|---|---|---|---|
| 4,520,007 A | | 5/1985 | Entwistle et al. |
| 4,783,481 A | | 11/1988 | Swaine |
| 4,788,297 A | | 11/1988 | Whittle |
| H852 H | * | 11/1990 | Garden et al. ............... 514/432 |
| 2005/0159450 A1 | * | 7/2005 | Dargazanli ........... C07D 211/26 514/317 |
| 2008/0260683 A1 | | 10/2008 | Bowman et al. |
| 2013/0231380 A1 | | 9/2013 | Bowman et al. |

FOREIGN PATENT DOCUMENTS

| | | |
|---|---|---|
| EP | 0 098629 | 1/1984 |
| EP | 0 147 052 | 7/1985 |
| EP | 0 175 466 | 3/1986 |
| WO | WO 2005/072524 | 8/2005 |
| WO | WO 2015/189320 | 12/2015 |

OTHER PUBLICATIONS

International Search Report, PCT/EP2016/079865, dated Jan. 27, 2017.
Written Opinion, PCT/EP2016,079865, dated Jan. 27, 2017.
Jae-Chul Jung et al: "Total synthesis of flocoumafen via Knoevenagel condensation and intramolecular ring cyclization: general access to natural products", Molecules: A Journal of Synthetic Organic and Natural Product Chemistry, M D P I AG, CH, vol. 17, No. 2, Feb. 21, 2012 (Feb. 21, 2012), pp. 2091-2102, XP002755590, ISSN: 1420-3049, DOI:10.3390/MOLECULES17022091 the whole document.

* cited by examiner

*Primary Examiner* — Susan T Tran
(74) *Attorney, Agent, or Firm* — Ipsilon USA, LLP (57) ABSTRACT

Disclosed is a composition including flocoumafen and an amount of a configurational stereoisomer of flocoumafen, named enantiomer $E_4$, such that the ratio of this amount to the amount of flocoumafen in the composition is less than 10%, the enantiomer $E_4$ being present with the exclusion of a racemic mixture, the enantiomer $E_4$ having, by chromatographic analysis of flocoumafen, a retention time $t_4$ having a value such that $t_1 < t_2 < t_3 < t_4$; $t_1$, $t_2$ and $t_3$ representing the retention times of the configurational stereoisomers of flocoumafen different from the enantiomer $E_4$, the chromatographic analysis being performed at a temperature of 23.5° C.

16 Claims, 1 Drawing Sheet

COMPOSITION AND RODENTICIDAL BAIT COMPRISING FLOCOUMAFEN, AND PROCESS FOR CONTROLLING TARGET RODENT PESTS

The invention relates to a composition comprising flocoumafen, to a rodenticidal bait comprising such a composition and to a process for controlling target rodent pests. The invention thus relates to the technical field of controlling the development of populations of target rodent pests.

It is known practice to use poisons in the form of rodenticidal baits against target rodent pests. WO 2005/072524 discloses a rodenticidal bait comprising a proportion of 50 ppm of flocoumafen in the bait and a proportion of 40 ppm of fipronil.

Such a bait is liable to be consumed by animals other than target rodent pests when it is made available to target rodent pests. It may be consumed directly (primary consumption) by domestic animals or pets. It may also be consumed accidentally by humans. Such consumption may induce poisoning, which may be lethal, of these domestic animals, pets or humans.

In addition, a fraction of the flocoumafen of these rodenticidal baits may be ingested (secondary consumption) by animals—especially by birds, in particular birds of prey—which prey or carrion-feed on rodent pests and especially weakened target rodent pests that have consumed such a rodenticidal bait. This secondary consumption is liable in the long term to result in the death of these predatory or carrion-feeding animals, which may be animals—especially birds—belonging to protected species.

The invention is thus directed towards overcoming these drawbacks by proposing a composition comprising flocoumafen, a rodenticidal bait comprising such a composition and a process for controlling target rodent pests, which are effective for controlling populations of target rodent pests and can also limit the risks of poisoning of non-target species, for example domestic animals or pets, or else humans, which may accidentally consume such rodenticidal baits.

The invention is also directed towards overcoming these drawbacks by proposing a composition comprising flocoumafen, a rodenticidal bait comprising such a composition and a process for controlling target rodent pests, which are effective for controlling populations of target rodent pests and can also limit the risks of poisoning by secondary consumption of domestic animals (pets or reared animals) or wild animals—for example foxes or birds—which prey on target rodent pests that have consumed the rodenticidal bait or which carrion-feed on the corpses of poisoned target rodent pests.

The invention is also directed towards proposing a composition comprising flocoumafen, a rodenticidal bait comprising such a composition and a process for controlling target rodent pests, the use of which is in accordance with the rules of good practice, especially with respect to the protection of birds, and in particular birds of prey.

The invention is also directed towards a composition comprising flocoumafen, a rodenticidal bait comprising such a composition and a process for controlling target rodent pests, which are environmentally friendly and friendly to human health and to the health of non-target animals.

The invention is also directed towards proposing a composition comprising flocoumafen, a rodenticidal bait comprising such a composition and a process for controlling target rodent pests, which are able to be used for controlling target rodent pests that are resistant to known baits for controlling target rodent pests. The invention is thus also directed towards proposing an alternative to known rodenticidal baits.

To do this, the invention relates to a composition comprising flocoumafen including an amount of a configurational stereoisomer of flocoumafen, named enantiomer $E_4$, such that the ratio of this amount to the amount of flocoumafen in the composition is less than 10%, said enantiomer $E_4$ having, by chromatographic analysis of a flocoumafen composition comprising four configurational stereoisomers of flocoumafen, a retention time $t_4$ having a value such that $t_1 < t_2 < t_3 < t_4$; $t_1$, $t_2$ and $t_3$ representing the retention times of the configurational stereoisomers of flocoumafen different from said enantiomer $E_4$; characterized in that the amount of said enantiomer $E_4$ in the composition is different from the amount of a configurational stereoisomer of flocoumafen, named enantiomer $E_1$, having, by chromatographic analysis of a flocoumafen composition under the abovementioned conditions, a retention time $t_1$ having a value such that $t_1 < t_2 < t_3 < t_4$;

the chromatographic analysis being performed at a temperature of 23.5° C. and under the conditions below:
  on a high-pressure liquid chromatography column of dimensions 150×2 mm, and comprising a chiral stationary phase constituted of particles of tris(4-chloro-3-methylphenyl carbamate) cellulose, said particles having a mean size of 3 µm and having a mean pore size of 1000 Å;
  using, as liquid mobile phase, a mixture formed from acetonitrile (A) and water comprising 0.1% by volume of formic acid (B), with an A/B volume ratio of 92/8 and with a flow rate of the liquid mobile phase in the chromatography column of 0.25 mL/minute;
  by injection into the chromatography column of a volume of 1 µL of flocoumafen composition at a concentration of 1 µg of flocoumafen per millilitre of acetonitrile.

Throughout the text:
  the term "flocoumafen" denotes the compound of formula 3-[4-(4-trifluoromethylbenzyloxy)phenyl-4-yl]-1-(4-hydroxycoumarin-3-yl)-1,2,3,4-tetrahydronaphthalene or 4-hydroxy-3-[1,2,3,4-tetrahydro-3-[4-[[4-(trifluoromethyl)phenyl]methoxy]phenyl]-1-naphthalenyl]-2H-1-benzopyran-2-one, or 4-hydroxy-3-[1,2,3,4-tetrahydro-3-[4-(4-trifluoromethylbenzyloxy)phenyl]-1-naphthyl]coumarin of formula (I) below:

in which are represented the numbers of carbons 1 and 3 of the 1,2,3,4-tetrahydronaphthalene group;
  the term "stereoisomers" denotes isomers of the same semi-structural formula, but in which the relative position of the atoms differs in space. The term "configurational stereoisomers" denotes stereoisomers for which conversion from one to the other of these configurational stereoisomers requires the cleavage/reformation of an interatomic covalent bond. Thus, the term "configurational stereoisomers" denotes stereoisomers which are not conformational isomers (or "rotamers", for which conversion from one to the other of the conformational isomers is accompanied only by rotation of a part of the molecule about the axis of a σ (sigma) bond formed by axial orbital overlap);

the term "amount" means a molar amount, a mass amount or a volume amount. The proportions are thus proportions of a molar amount relative to a molar amount, of a mass amount relative to a mass amount, or of a volume amount relative to a volume amount;

the term "substantially" indicates, in the usual manner, that a structural or functional characteristic should not be taken as marking an abrupt discontinuity, which would have no physical meaning, but covers not only this structure or this function, but also slight variations of this structure or of this function which produce, in the technical context under consideration, an effect of the same nature, or else of the same degree;

the expressions "high-pressure liquid chromatography" or "high-performance liquid chromatography" (HPLC) denote "HPLC" chromatography or "High Performance Liquid Chromatography"; and the term "retention time" denotes the time, measured at the top of the peak in the chromatogram, for which a compound is retained on a chromatography column.

The inventors have observed that analysis of flocoumafen by high-pressure liquid chromatography under the conditions described above reveals four signals or peaks corresponding to four compounds of the same chemical structural formula and corresponding to formula (I) of flocoumafen. They determined, by analysis of flocoumafen preparations comprising variable proportions of the two diastereoisomers of flocoumafen, that:

the compound corresponding to the signal with a retention time $t_1$ having a value of the order of 4.5 minutes is one configurational stereoisomer, named enantiomer $E_1$, of one of the two diastereoisomers, named diastereoisomer $D_{1,4}$, of flocoumafen;

the compound corresponding to the signal with a retention time $t_2$ having a value of the order of 6.2 minutes is one configurational stereoisomer, named enantiomer $E_2$, of the other diastereoisomer, named diastereoisomer $D_{2,3}$, of flocoumafen, different from said diastereoisomer $D_{1,4}$;

the compound corresponding to the signal with a retention time $t_3$ having a value of the order of 6.8 minutes is the other configurational stereoisomer, named enantiomer $E_3$, of said diastereoisomer $D_{2,3}$, different from said enantiomer $E_2$; and the compound corresponding to the signal with a retention time $t_4$ having a value of the order of 9.3 minutes is the other configurational stereoisomer, named enantiomer $E_4$, of said diastereoisomer $D_{1,4}$, different from said enantiomer $E_1$.

The retention time values $t_1$, $t_2$, $t_3$ and $t_4$ are liable to vary, especially with the temperature of the chromatography column. However, under these chromatographic conditions, the order of elution of the configurational stereoisomers of flocoumafen remains unchanged.

One of the two diastereoisomers of flocoumafen is a configurational stereoisomer of flocoumafen in which carbons 1 and 3 of the 1,2,3,4-tetrahydronaphthalene group of flocoumafen have the same absolute configuration and the other of the two diastereoisomers of flocoumafen is a configurational stereoisomer of flocoumafen in which carbons 1 and 3 of the 1,2,3,4-tetrahydronaphthalene group of flocoumafen have different absolute configurations, the absolute configurations being determined according to the Cahn-Ingold-Prelog sequential priority and nomenclature rules.

The inventors performed such a separation of the configurational stereoisomers, i.e. of the enantiomers of the two diastereoisomers, of flocoumafen by high-pressure liquid chromatography on a LUX® Cellulose-4 chiral column (00F-4490-B0, Phenomenex, Le Pecq, France). Where appropriate, it is possible successively to perform several high-pressure liquid chromatography steps on a chiral column for the purposes of obtaining the desired amount of configurational stereoisomer of flocoumafen in the desired purity. The inventors obtained each configurational stereoisomer purified and separated from the other configurational stereoisomers of flocoumafen by removal of the mobile phase of the collected fraction. They discovered that it is also possible to perform such a separation by high-pressure liquid chromatography on a preparative chiral column of larger dimensions—especially with an inside diameter of greater than 2 mm—and in which the stationary phase has a particle size of greater than 3 µm.

A method for separating the enantiomers of said diastereoisomer $D_{1,4}$ of flocoumafen and of said diastereoisomer $D_{2,3}$ of flocoumafen was not previously known. Under these experimental conditions, the enantiomers ($E_1$ and $E_4$) of said diastereoisomer $D_{1,4}$ and the enantiomers ($E_2$ and $E_3$) of said diastereoisomer $D_{2,3}$ are efficiently separated and purified by high-pressure liquid chromatography.

The inventors succeeded in separating said enantiomer $E_4$ and the other configurational stereoisomers of flocoumafen different from said enantiomer $E_4$, and in preparing a composition according to the invention in which the amount of said enantiomer $E_4$ is such that its ratio to the amount of flocoumafen in the composition is less than 10%.

The inventors who succeeded in separating the enantiomers of each diastereoisomer of flocoumafen also observed, entirely surprisingly, that these enantiomers do not all have the same persistence in the liver of target rodent pests and that said enantiomer $E_4$ is more persistent in the liver of target rodent pests than are said enantiomer $E_1$ of said diastereoisomer $D_{1,4}$ and enantiomers $E_2$ and $E_3$ of said diastereoisomer $D_{2,3}$.

They thus observed that said enantiomer $E_4$ is in fact the configurational stereoisomer of flocoumafen which is accumulated the most in the liver of dead or live target rodent pests which have ingested flocoumafen. Such target rodent pests which have accumulated said enantiomer $E_4$ constitute poisoned prey that are toxic for non-rodent mammals and birds which consume at least one such target rodent pest—dead or live—and in particular for predators (especially non-rodent mammals and birds) which preferentially consume the viscera of their prey and in particular the liver of their prey. Said enantiomer $E_4$ is thus the configurational stereoisomer of flocoumafen that is the most toxic with respect to non-target animals and the environment.

The invention thus relates to a composition comprising flocoumafen in which the ratio of the amount of said enantiomer $E_4$ that is the most retained (which has the longest retention time of the retention times of the four configurational stereoisomers of flocoumafen) on a chromatography column under the abovementioned conditions to the amount of flocoumafen is less than 10%.

The invention thus relates to a composition comprising flocoumafen in which the amount of the configurational stereoisomer of flocoumafen with the highest persistence in the liver of target rodent pests is such that the ratio of this amount to the amount of flocoumafen in the composition is less than 10%.

A composition and a rodenticidal bait according to the invention comprising an amount of said enantiomer $E_4$ such that the ratio of this amount to the amount of flocoumafen in the composition or in the bait is less than 10% in fact make it possible, entirely surprisingly, to efficiently control target rodent pests.

Advantageously and in one embodiment according to the invention, the amount of said enantiomer $E_4$ in the composition is such that the ratio of this amount to the amount of flocoumafen in the composition is less than 8%, especially less than 5%, preferably less than 3%, more preferentially less than 2% and even more preferentially less than 1%.

Advantageously and in another embodiment according to the invention, the composition may be substantially free of said enantiomer $E_4$, i.e. said enantiomer $E_4$ may be present in the composition but only in trace amount.

Advantageously and according to the invention, the composition is free of said enantiomer $E_4$. A particular aspect of the invention thus relates to a composition comprising flocoumafen, which is substantially—in particular totally—free of said enantiomer $E_4$.

Advantageously and according to the invention, the amount of said enantiomer $E_4$ in the composition is different from the amount of a configurational stereoisomer of flocoumafen, named enantiomer $E_1$, having, by chromatographic analysis of a flocoumafen composition under the abovementioned conditions, a retention time $t_1$ having a value such that $t_1<t_2<t_3<t_4$. The invention is thus directed towards a composition, a rodenticidal bait and a process for controlling target rodent pests, in which said enantiomer $E_4$ is present, with the exclusion of a racemic mixture. In a composition, a rodenticidal bait and a process for controlling target rodent pests according to the invention, said enantiomer $E_4$ and said enantiomer $E_1$ are not in racemic mixture.

Advantageously and according to the invention, the composition comprises an amount of a configurational stereoisomer of flocoumafen, named enantiomer $E_2$, which has, by chromatographic analysis of a flocoumafen composition comprising four configurational stereoisomers of flocoumafen performed under the abovementioned conditions, a retention time $t_2$ having a value such that $t_1<t_2<t_3<t_4$, the amount of said enantiomer $E_2$ being such that the ratio of this amount to the amount of flocoumafen in the composition is less than 10%.

Advantageously and according to the invention, the amount of said enantiomer $E_2$ in the composition is such that the ratio of this amount to the amount of flocoumafen in the composition is less than 8%, especially less than 5%, preferably less than 3%, more preferentially less than 2% and even more preferentially less than 1%.

Advantageously and according to the invention, the composition may be substantially free of said enantiomer $E_2$, i.e. said enantiomer $E_2$ may be present in the composition but only in trace amount. Advantageously and according to the invention, the composition is free of said enantiomer $E_2$.

The invention thus relates to a composition comprising flocoumafen, which is substantially—in particular totally—free of said enantiomer $E_4$ of flocoumafen and which is also substantially—in particular totally—free of said enantiomer $E_2$ of flocoumafen.

According to another aspect of the invention, the composition may comprise an amount of said enantiomer $E_2$ such that the ratio of this amount to the amount of flocoumafen in the composition is between 30% and 100%, especially between 90% and 100% (limit inclusive).

Advantageously and according to the invention, the composition comprises an amount of a configurational stereoisomer of flocoumafen, named enantiomer $E_3$, which has, by chromatographic analysis of a flocoumafen composition comprising four configurational stereoisomers of flocoumafen performed under the abovementioned conditions, a retention time $t_3$ having a value such that $t_1<t_2<t_3<t_4$, the amount of said enantiomer $E_3$ being such that the ratio of this amount to the amount of flocoumafen in the composition is less than 10%.

Advantageously and according to the invention, the amount of said enantiomer $E_3$ in the composition is such that the ratio of this amount to the amount of flocoumafen in the composition is less than 8%, especially less than 5%, preferably less than 3%, more preferentially less than 2% and even more preferentially less than 1%.

Advantageously and according to the invention, the composition may be substantially free of said enantiomer $E_3$, i.e. said enantiomer $E_3$ may be present in the composition but only in trace amount. Advantageously and according to the invention, the composition is free of said enantiomer $E_3$.

The invention thus relates to a composition comprising flocoumafen, which is substantially—in particular totally—free of said enantiomer $E_4$ of flocoumafen and which is also substantially—in particular totally—free of said enantiomer $E_2$ of flocoumafen, and which is also substantially—in particular totally—free of said enantiomer $E_3$ of flocoumafen.

According to another particular aspect of the invention, the composition may comprise an amount of said enantiomer $E_3$ such that the ratio of this amount to the amount of flocoumafen in the composition is between 30% and 100%, especially between 90% and 100% (limit inclusive).

Advantageously and as a variant according to the invention, the composition comprises said enantiomer $E_2$ and said enantiomer $E_3$, with the exclusion of a racemic mixture of said enantiomer $E_2$ and of said enantiomer $E_3$. However, in another variant according to the invention, said enantiomer $E_2$ and said enantiomer $E_3$ are in equimolar amount in the composition. The composition thus comprises a racemic mixture of said enantiomer $E_2$ and of said enantiomer $E_3$.

Advantageously and according to the invention, the composition comprises an amount of a configurational stereoisomer of flocoumafen, named enantiomer $E_1$, which has, by chromatographic analysis of a flocoumafen composition comprising four configurational stereoisomers of flocoumafen performed under the abovementioned conditions, a retention time $t_1$ having a value such that $t_1<t_2<t_3<t_4$, the ratio of the amount of said enantiomer $E_1$ in the composition to the amount of flocoumafen in the composition being between 30% (limit inclusive) and 100% (limit inclusive), especially between 90% (limit inclusive) and 100% (limit inclusive).

Advantageously and according to the invention, the composition is in liquid form and comprises a liquid solvent for flocoumafen. It may also be a solution of flocoumafen in a solvent for flocoumafen. It may also be a solid comprising flocoumafen.

The invention also relates to a chromatographic process for separating the configurational stereoisomers of flocoumafen. The invention thus relates to such a chromatographic process for separating the configurational stereoisomers of flocoumafen, in which:

a high-pressure liquid chromatography column of dimensions 150×2 mm, and comprising a chiral stationary phase constituted of particles of tris(4-chloro-3-methylphenyl carbamate) cellulose, is chosen, said particles having a mean size of 3 μm and having a mean pore size of 1000 Å;

a mixture formed from acetonitrile (A) and water comprising 0.1% by volume of formic acid (B), with an A/B volume ratio of 92/8 and with a flow rate of the liquid mobile phase in the chromatography column of 0.25 mL/minute, is chosen as liquid mobile phase;

separation of the configurational stereoisomers is performed at room temperature, during which:

a liquid composition comprising configurational stereoisomers of flocoumafen is introduced into the top of the chromatography column; and then the liquid composition is entrained with the mobile phase in the chromatography column under conditions suitable for separating the configurational stereoisomers of flocoumafen, and a plurality of fractions of the mobile phase are collected, each fraction comprising one of the configurational stereoisomers of flocoumafen separately from the other configurational stereoisomers of flocoumafen; and the liquid mobile phase of each fraction is removed so as to obtain each configurational stereoisomer.

The invention also relates to a configurational stereoisomer of flocoumafen obtained via a process according to the invention.

The invention also relates to the use of a composition according to the invention for the preparation of a rodenticidal bait for target rodent pests.

The invention also relates to a rodenticidal bait comprising a composition according to the invention, and at least one excipient that is edible for target rodent pests.

A rodenticidal bait according to the invention comprises:
at least one excipient that is edible for target rodent pests,
an amount of a configurational stereoisomer of flocoumafen, named enantiomer $E_4$, such that the ratio of this amount to the amount of flocoumafen in the composition is less than 10%, said enantiomer $E_4$ having, by chromatographic analysis of a flocoumafen composition comprising four configurational stereoisomers of flocoumafen, a retention time $t_4$ having a value such that $t_1<t_2<t_3<t_4$; $t_1$, $t_2$ and $t_3$ representing the retention times of the configurational stereoisomers of flocoumafen different from said stereoisomer $E_4$;
characterized in that the amount of said enantiomer $E_4$ in the composition is different from the amount of a configurational stereoisomer of flocoumafen, named enantiomer $E_1$, having, by chromatographic analysis of a flocoumafen composition under the abovementioned conditions, a retention time $t_1$ having a value such that $t_1<t_2<t_3<t_4$;
the chromatographic analysis being performed at a temperature of 23.5° C. and under the conditions below:
on a high-pressure liquid chromatography column of dimensions 150×2 mm, and comprising a chiral stationary phase constituted of particles of tris(4-chloro-3-methylphenyl carbamate) cellulose, said particles having a mean size of 3 μm and having a mean pore size of 1000 Å;
using, as liquid mobile phase, a mixture formed from acetonitrile (A) and water comprising 0.1% by volume of formic acid (B), with an A/B volume ratio of 92/8 and with a flow rate of the liquid mobile phase in the chromatography column of 0.25 mL/minute;
by injection into the chromatography column of a volume of 1 μL of flocoumafen composition at a concentration of 1 μg of flocoumafen per millilitre of acetonitrile.

Advantageously, a rodenticidal bait according to the invention comprises an excipient that is edible for target rodent pests and an amount of said enantiomer $E_4$ such that the ratio of this amount to the amount of flocoumafen in the rodenticidal bait is less than 10%.

Such a bait is rodenticidal and also makes it possible to limit the residual amount of flocoumafen in the liver of target rodent pests. Such a rodenticidal bait is thus less toxic to the environment, and in particular to animals—especially birds belonging to protected species—which prey or carrion-feed on rodent pests and especially on weakened target rodent pests which have consumed such a rodenticidal bait.

They also observed that a bait according to the invention is able to be used to control populations of target rodent pests that are resistant to known rodenticidal treatments.

Advantageously and according to the invention, the rodenticidal bait comprises an amount of a configurational stereoisomer of flocoumafen, named enantiomer $E_2$, which has, by chromatographic analysis of a flocoumafen composition comprising four configurational stereoisomers of flocoumafen performed under the abovementioned conditions, a retention time $t_2$ having a value such that $t_1<t_2<t_3<t_4$, the amount of said enantiomer $E_2$ being such that the ratio of this amount to the amount of flocoumafen in the composition is less than 10%.

Advantageously and according to the invention, the rodenticidal bait comprises an amount of a configurational stereoisomer of flocoumafen, named enantiomer $E_3$, which has, by chromatographic analysis of a flocoumafen composition comprising four configurational stereoisomers of flocoumafen performed under the abovementioned conditions, a retention time $t_3$ having a value such that $t_1<t_2<t_3<t_4$, the amount of said enantiomer $E_3$ being such that the ratio of this amount to the amount of flocoumafen in the composition is less than 10%.

Advantageously and according to the invention, the rodenticidal bait comprises an amount of a configurational stereoisomer of flocoumafen, named enantiomer $E_1$, which has, by chromatographic analysis of a flocoumafen composition comprising four configurational stereoisomers of flocoumafen performed under the abovementioned conditions, a retention time $t_1$ having a value such that $t_1<t_2<t_3<t_4$, the amount of said enantiomer $E_1$ being such that the ratio of this amount to the amount of flocoumafen in the composition is between 90% (limit inclusive) and 100% (limit inclusive).

Advantageously, a rodenticidal bait according to the invention comprises a mass amount of flocoumafen such that the ratio of this mass amount of flocoumafen to the mass amount of rodenticidal bait is less than 200 ppm, i.e. less than 200 mg of flocoumafen per kilogram of rodenticidal bait. Advantageously, it comprises a mass amount of flocoumafen such that the ratio of this mass amount of flocoumafen to the mass amount of bait is between 1 ppm and 200 ppm (1 mg to 200 mg of flocoumafen per kilogram of rodenticidal bait). Advantageously, a rodenticidal bait according to the invention comprises a mass amount of flocoumafen such that the ratio of this mass amount of flocoumafen to the mass amount of bait is between 1 ppm and 100 ppm (1 mg to 100 mg of flocoumafen per kilogram of rodenticidal bait), especially between 1 ppm and 50 ppm (1 mg to 50 mg of flocoumafen per kilogram of rodenticidal bait), preferably between 10 ppm and 25 ppm (10 mg to 25 mg of flocoumafen per kilogram of rodenticidal bait).

Advantageously and according to the invention, the excipient that is edible for target rodent pests is chosen to allow consumption of the rodenticidal bait by target rodent pests. Advantageously and according to the invention, each edible excipient is non-lethal to target rodent pests. The edible excipient is not in itself rodenticidal.

Advantageously and according to the invention, the edible excipient comprises at least one food chosen from the group formed from cereal seeds—especially hulled cereal seeds—cereal seed meals, cereal seed flours, cereal seed flakes, cereal bran and non-cereal seeds, for example alfalfa seeds—especially in hulled form, in the form of meal, in the form of flour, or in the form of flakes or bran. The edible excipient may comprise any support that can be consumed by target rodent pests.

Advantageously, the edible excipient comprises at least one food chosen from the group formed from foods of plant origin and foods of animal origin. Advantageously, the edible excipient comprises at least one food chosen to be able to stimulate the appetite of the target rodent pests. In particular, this food is chosen from the group formed from seeds of one or more cereals, hulled seeds of one or more cereals, meals of seeds of one or more cereals, flakes of seeds of one or more cereals, bran of one or more cereals and flour of seeds of one or more cereals. By way of example, the cereals are chosen from the group formed from oat, wheat, barley, corn, soybean and rice.

Advantageously, the food is chosen from the group formed from sweetened foods. For example, they may be foods comprising at least one sugar chosen from the group formed from sucrose, lactose, fructose and glucose. It may be a sugar syrup—for example a sugar syrup obtained by hydrolysis of starch—or a sugar syrup obtained by hydrolysis of sucrose (invert sugar syrup), or a beet sugar syrup, or a maple syrup or a sugarcane syrup, or a syrup obtained from a plant of the *Stevia* genus.

Advantageously, the food is chosen from the group formed from coconut albumen (copra) flakes and flour. Advantageously, the food is chosen from the group formed from walnuts, hazelnuts and almonds—in grated and/or powder form.

Advantageously, the food is chosen from the group formed from plant fats, plant oils (for example rapeseed oil, soybean fat, sunflower oil, cocoa butter, groundnut oil, groundnut butter, corn oil, palm oil), animal fats and animal oils (butter, lard, fish oil).

Advantageously, the food is chosen from the group formed from proteins of plant origin and proteins of animal origin. By way of example, examples that may be mentioned include powdered milk—especially powdered skimmed milk—eggs—especially powdered eggs—protein hydrolysates of animal origin and protein hydrolysates of plant origin.

Advantageously and according to the invention, the rodenticidal bait is chosen from the group formed from solid baits comprising flocoumafen and a solid edible excipient. Advantageously, the rodenticidal bait is a solid in divided form, for example in the form of balls or granules. Advantageously, the rodenticidal bait may be a solid in block or paste form that may be consumed by the target rodent pests or a solid material that may be nibbled by the target rodent pests. Advantageously, the solid rodenticidal bait according to the invention may be in the form of a rigid block, a semi-rigid block, a foam, a powder or a gel.

Advantageously, the rodenticidal bait which is in the form of a powder, in the form of a foam or in the form of a gel is suitable for soiling the fur of the target rodent pest(s) and for being ingested by said pest(s) during their grooming.

Advantageously and according to the invention, the rodenticidal bait is chosen from the group formed from liquid baits comprising flocoumafen and a liquid edible excipient. The rodenticidal bait is then a drink for target rodent pests. It may also be a suspension of flocoumafen in solid form in a liquid medium. It may also be an emulsion of flocoumafen in a liquid medium.

Advantageously, the rodenticidal bait comprises at least one dye. Such a dye makes it possible in particular to give said rodenticidal bait a colour that is readily detectable and identifiable by a person handling the rodenticidal bait.

Advantageously, the rodenticidal bait comprises at least one preserving agent capable of ensuring its conservation during its storage. Advantageously, the rodenticidal bait comprises at least one bittering compound such as denatonium benzoate, also known as Bitrex®, which is intended to reduce the risks of accidental consumption by non-target organisms.

Advantageously, in one particular variant, the composition and the rodenticidal bait according to the invention exclusively comprise flocoumafen as rodenticidal substance. In particular, the composition and the rodenticidal bait according to the invention are free of any other anticoagulant substance for rodenticidal use different from flocoumafen. However, in this variant according to the invention, the composition and the rodenticidal bait may comprise any pest-control substance other than a rodenticide, such as an insecticidal and/or acaricidal substance.

Advantageously, in another particular variant, the composition and the rodenticidal bait according to the invention comprise flocoumafen, with the exclusion of a racemic mixture of the two enantiomers $E_1$ and $E_4$, and at least one other substance different from flocoumafen as rodenticidal substance. This other rodenticidal substance different from flocoumafen may be another anticoagulant substance—especially of the anti-vitamin K type or not—or any other non-anticoagulant rodenticidal substance.

The invention also relates to a process for controlling target rodent pests, in which there is spread an amount of rodenticidal bait comprising:
  at least one excipient that is edible for target rodent pests,
  an amount of a configurational stereoisomer of flocoumafen, named enantiomer $E_4$, such that the ratio of this amount to the amount of flocoumafen in the composition is less than 10%, said enantiomer $E_4$ having, by chromatographic analysis of a flocoumafen composition comprising four configurational stereoisomers of flocoumafen, a retention time $t_4$ having a value such that $t_1<t_2<t_3<t_4$; $t_1$, $t_2$ and $t_3$ representing the retention times of the configurational stereoisomers of flocoumafen different from said stereoisomer $E_4$;
characterized in that the amount of said enantiomer $E_4$ in the composition is different from the amount of a configurational stereoisomer of flocoumafen, named enantiomer $E_1$, having, by chromatographic analysis of a flocoumafen composition under the abovementioned conditions, a retention time $t_1$ having a value such that $t_1<t_2<t_3<t_4$;
the chromatographic analysis being performed at a temperature of 23.5° C. and under the conditions below:
  on a high-pressure liquid chromatography column of dimensions 150×2 mm, and comprising a chiral stationary phase constituted of particles of tris(4-chloro-3-methylphenyl carbamate) cellulose, said particles having a mean size of 3 µm and having a mean pore size of 1000 Å;

using, as liquid mobile phase, a mixture formed from acetonitrile (A) and water comprising 0.1% by volume of formic acid (B), with an A/B volume ratio of 92/8 and with a flow rate of the liquid mobile phase in the chromatography column of 0.25 mL/minute;

by injection into the chromatography column of a volume of 1 µL of flocoumafen composition at a concentration of 1 µg of flocoumafen per millilitre of acetonitrile.

The invention relates to a process for controlling target rodent pests, in which there is spread an amount of rodenticidal bait according to the invention, said amount of bait being sufficient to be rodenticidal.

Advantageously and as a variant according to the invention, the following are chosen in combination:
the edible excipient;
an amount of said enantiomer $E_4$ relative to the flocoumafen;
a mass proportion of flocoumafen in the rodenticidal bait; and
an amount of spread rodenticidal bait;
so that target rodent pests consume an amount of flocoumafen that is sufficient to be lethal to said target rodent pests which consume said rodenticidal bait in the course of a single period of 24 consecutive hours.

A rodenticidal bait according to this variant of the invention is a rodenticidal bait that is mortal in a single intake, or a "one-shot" bait. Advantageously and according to this variant of the invention, the mass proportion of flocoumafen in the rodenticidal bait is less than 200 ppm, especially between 2 ppm and 200 ppm, preferably between 2 ppm and 100 ppm, more preferentially between 2 ppm and 50 ppm and in particular between 15 ppm and 50 ppm.

Advantageously and in another variant according to the invention, the following are chosen in combination:
the edible excipient;
an amount of said enantiomer $E_4$ relative to the flocoumafen;
a mass proportion of flocoumafen in the rodenticidal bait; and
an amount of spread rodenticidal bait;
so that target rodent pests consume an amount of flocoumafen:
which is non-lethal to target rodent pests, i.e. which is generally non-lethal to target rodent pests which consume said rodenticidal bait over a single period of 24 consecutive hours; and
which is sufficient to be lethal to target rodent pests which consume said rodenticidal bait over a plurality of 24-hour periods.

Advantageously, the 24-hour periods of the plurality of 24-hour periods are consecutive.

This other variant of the invention is thus also directed towards a process for controlling target rodent pests, in which there is spread an amount of rodenticidal bait that is lethal for target rodent pests which durably consume this rodenticidal bait and generally non-lethal for non-target rodents or animals which accidentally consume this rodenticidal bait. This is then referred to as a "multi-dose" or "multi feeding" control process. In such a process according to the invention, the consumption of rodenticidal bait by a target rodent pest over a period of 24 hours is insufficient to result in the death of said rodent, whereas repeated consumption of rodenticidal bait over at least two consecutive days can result in the death of the target rodent pest.

This other variant of the invention is thus directed towards a process for controlling a population of target rodent pests, in which target rodent pests are provided with an amount of rodenticidal bait that is liable to be ingested by the target rodent pests, said amount of rodenticidal bait being sufficient to kill target rodent pests which daily consume said rodenticidal bait over several days, especially over at least two 24-hour periods, especially from 3 to 7 periods, said periods being consecutive.

Advantageously, in this other variant of a process according to the invention, the mass proportion of flocoumafen relative to the rodenticidal bait is between 2 ppm and 100 ppm, especially between 2 ppm and 50 ppm, in particular between 2 ppm and 15 ppm, especially about 10 ppm.

In a process according to the invention, a rodenticidal bait according to the invention and the amount of rodenticidal bait spread are chosen so as to allow consumption of rodenticidal bait over several days by target rodent pests, while at the same time limiting:
the risks of primary intoxication of non-target mammals and birds which are liable to consume such a rodenticidal bait only occasionally and accidentally;
the risks of secondary intoxication, for example of predators of target rodents, which are liable to consume target rodents—dead or live—that have ingested an amount of said rodenticidal bait.

The invention also relates to a composition comprising flocoumafen, to a rodenticidal bait comprising such a composition, to a process for separating configurational stereoisomers of flocoumafen and to a process for controlling target rodent pests, which are characterized in combination by all or some of the characteristics mentioned hereinabove or hereinbelow.

Other aims, characteristics and advantages of the invention will emerge on reading the following description and the examples, which are given for purely non-limiting purposes and which refer to the attached figures, in which.

ANALYSIS OF THE CONFIGURATIONAL STEREOISOMERS OF FLOCOUMAFEN

The configurational stereoisomers of flocoumafen are separated by high-pressure liquid chromatography using a LUX® Cellulose-4 chiral column (00F-4490-B0, Phenomenex, Le Pecq, France) as stationary phase and a mixture formed from acetonitrile (A) and water comprising 0.1% by volume of formic acid (B), with an A/B volume ratio of 92/8, as mobile phase with a flow rate of the liquid mobile phase in the chromatography column of 0.25 mL/minute. 1 µL of extract comprising flocoumafen at a concentration of 1 µg/mL of acetonitrile is injected. Detection is performed by tandem mass spectrometry (MS/MS) in negative electrospray ionization (ESI) mode. The temperature of the nebulizer gas is 350° C. and its flow rate is 8 L/minute. The pressure of the nebulizer gas is brought to 2700 hPa. In particular, the MRM ("Multiple Reaction Monitoring") transitions m/z 541.1→382.1 and m/z 541.1→161, corresponding to the flocoumafen signal, are analysed.

The retention time values for each of the flocoumafen enantiomers are, under the conditions described:
$t_1$=4.5 min for said enantiomer $E_1$ of said diastereoisomer $D_{1,4}$;
$t_2$=6.2 min for said enantiomer $E_2$ of said diastereoisomer $D_{2,3}$;
$t_3$=6.7 min for said enantiomer $E_3$ of said diastereoisomer $D_{2,3}$; and $t_4 = 9.3$ min for said enantiomer $E_4$ of said diastereoisomer $D_{1,4}$.

The retention time values $t_1$, $t_2$, $t_3$ and $t_4$ are liable to vary, especially with the temperature of the chromatography column. However, under these chromatographic conditions, the order of elution of the flocoumafen enantiomers remains unchanged. As a guide, the retention time value ($t_1$) of enantiomer $E_1$ of said diastereoisomer $D_{1,4}$ may range between 4.4 min and 4.6 min. The retention time value ($t_2$) of enantiomer $E_2$ of said diastereoisomer $D_{2,3}$ may range between 5.9 min and 6.4 min. The retention time value ($t_3$) of enantiomer $E_3$ of said diastereoisomer $D_{2,3}$ may range between 6.4 min and 6.9 min. The retention time value ($t_4$) of said enantiomer $E_4$ according to the invention may range between 8.9 min and 9.4 min.

Extraction of Flocoumafen from the Liver of Rats Tube-Fed with Flocoumafen

Homogenization of the Liver Sample

About 0.525 g (±0.025 g) of rat liver is weighed out accurately and placed in a 50 mL polypropylene tube. 10 mL of acetone are added and the suspension is homogenized using an Ultra-Turrax® homogenizer/disperser for a time of about 30 seconds. The homogenizer/disperser shaft is rinsed with hot water and then twice with 20 mL of acetone in a polypropylene tube. The homogenate is centrifuged for 5 minutes at a centrifugation speed of 3000 rpm (revolutions per minute). The supernatant is collected and transferred into a test tube. The sample is subjected to evaporation under a stream of nitrogen ($N_2$) at a temperature of 40° C. so as to form a dry extract.

Lipid Removal 1 mL of acetonitrile is added to the tube containing the dry extract so as to dissolve it. The acetonitrile solution is washed twice successively with 1 mL of hexane. The lipid-free extract is dried under a stream of nitrogen ($N_2$) at a temperature of 40° C. and is then taken up in 0.5 mL of methanol and dissolved by vortex stirring. 0.5 mL of ultra-pure (Milli-Q) water is then added. The sample is vortex-homogenized.

Solid-Phase Extraction (SPE) of Flocoumafen 1 mL of dichloromethane ($CH_2Ct_2$), then 1 mL of methanol ($CH_3OH$), then 1 mL of ultra-pure (Milli-Q) water are passed through an Oasis HLB 1 cc cartridge (WAT094225, Waters). The lipid-free liver extract (1 mL MeOH/Milli-Q $H_2O$) containing flocoumafen is then loaded onto the top of the cartridge beforehand. The liver extract penetrates through the cartridge by gravity on contact with the solid phase of the cartridge. 1 mL of washing solution formed from methanol ($CH_3OH$) and ultra-pure water ($H_2O$) in a 90/10 volume proportion is loaded onto the top of the cartridge. The cartridge is dried by suction under vacuum connected to the bottom of the cartridge. 1 mL of eluting solution formed from dichloromethane ($CH_2Cl_2$) and methanol ($CH_3OH$) in a 90/10 volume proportion is then loaded onto the top of the cartridge and an eluate comprising flocoumafen is collected at the bottom of the cartridge. The solvent of the eluate is evaporated off under a stream of nitrogen ($N_2$) at a temperature of 40° C. The sample is taken up in 0.5 mL of acetonitrile (NC—$CH_3$) and the acetonitrile solution containing flocoumafen is filtered through a 0.2 μm porosity filter.

Hepatic Persistence of the Configurational Stereoisomers ($E_1$, $E_2$, $E_3$ and $E_4$) of Flocoumafen in Rats A solution comprising flocoumafen in a mixture of vegetable oil and 5% of DMSO so that the amount of flocoumafen ingested by each rat is about 2.3 mg per kilogram of rat is administered orally (per os) to 8-week-old male and female laboratory rats (Sprague-Dawley rats, Charles River, Saint-Germain-sur-l'Arbresle, France) weighing between 180 and 200 g. The tube-fed rats are treated daily by subcutaneous administration of a dose of vitamin K1 at a rate of 1 U per rat so as to keep the rats alive throughout the experiment.

The ratio of the sum of the amounts of said enantiomer $E_2$ and of said enantiomer $E_3$ (diastereoisomer $D_{2,3}$) to the amount of flocoumafen in the tube-feeding solution is 59% and the ratio of the sum of the amounts of said enantiomer $E_1$ and of said enantiomer $E_4$ (diastereoisomer $D_{1,4}$) to the amount of flocoumafen in the tube-feeding solution is 41%.

At 1 day (D+1), 3 days (D+3) and 7 days (D+7) after tube-feeding, three male rats and three female rats anaesthetized beforehand with isoflurane are euthanized, the liver of the sacrificed rats is removed and the amounts of each of the configurational stereoisomers of flocoumafen present in the liver of the tube-fed male and female rats are then extracted from the liver and assayed. The results obtained on the male rats are given in table 1 below and the results obtained on the female rats are given in table 2 below in which the values of the concentration of each of the configurational stereoisomers of flocoumafen in the liver are the mean of the values measured on three rats expressed in nanograms (ng) per gram of liver.

TABLE 1

| (male rats) | | | |
|---|---|---|---|
| Hepatic concentration, ng/g | D + 1 | D + 3 | D + 7 |
| Enantiomer $E_1$ | 196 | 47 | 0 |
| Enantiomer $E_2$ | 3904 | 1962 | 319 |
| Enantiomer $E_3$ | 3301 | 1862 | 647 |
| Enantiomer $E_4$ | 8143 | 9906 | 2623 |

TABLE 2

| (female rats) | | | |
|---|---|---|---|
| Hepatic concentration, ng/g | D + 1 | D + 3 | D + 7 |
| Enantiomer $E_1$ | 4585 | 2692 | 1196 |
| Enantiomer $E_2$ | 5396 | 2522 | 469 |
| Enantiomer $E_3$ | 5478 | 2734 | 1228 |
| Enantiomer $E_4$ | 10342 | 7765 | 5054 |

Figure 1:
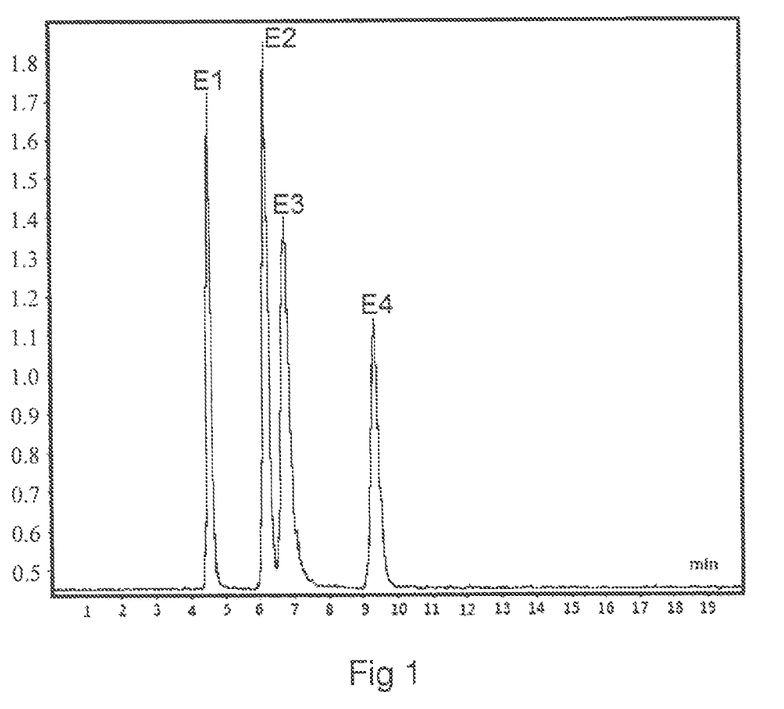
FIG. 1 is a representative chromatogram of the separation of the enantiomers of flocoumafen on a chiral column.
Figure 2:
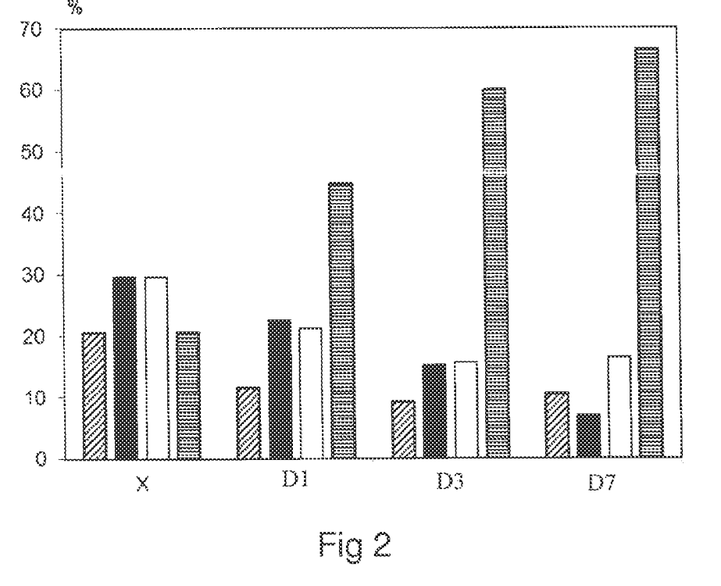
FIG. 2 is a histogram graph representation of the persistence of the enantiomers of flocoumafen in rat liver.

FIG. 2 represents the change in the percentage of the mass amount of each enantiomer ($E_1$ and $E_4$) of diastereoisomer $D_{1,4}$ and of each enantiomer ($E_2$ and $E_3$) of diastereoisomer $D_{2,3}$ relative to the amount of flocoumafen retained in the liver of the tube-fed rats (male and female) sacrificed on D+1, D+3 and D+7. The percentage of said enantiomer $E_1$ is represented by oblique-hatched columns, the percentage of said enantiomer $E_4$ is represented by horizontally-hatched columns, the percentage of said enantiomer $E_2$ is represented by black columns and the percentage of said enantiomer $E_3$ is represented by white columns. The respective proportions of each of the enantiomers ($E_1$ and $E_4$) of diastereoisomer $D_{1,4}$ and of the enantiomers ($E_2$ and $E_3$) of diastereoisomer $D_{2,3}$ in the flocoumafen of the tube-feeding composition are represented in column "X" FIG. 2 and are 20.5% for enantiomer $E_1$ of said diastereoisomer $D_{1,4}$ and 20.5% for enantiomer $E_4$ of said diastereoisomer $D_{1,4}$ and 29.5% for said enantiomer $E_2$ and 29.5% for said enantiomer $E_3$. Said enantiomer $E_4$ is the flocoumafen enantiomer that is the most persistent in rat liver and the most toxic to the environment.

The invention is thus directed towards a composition, a rodenticidal bait and a process for controlling target rodent pests comprising a small content of enantiomer $E_4$ different from the content of enantiomer $E_1$.

It goes without saying that the invention may be the subject of numerous implementation variants and applications. In particular, a composition, a rodenticidal bait and a process for controlling target rodent pests are subject to an infinite number of variants both in the formulation of the rodenticidal bait and in the embodiments of the process.

The invention claimed is:

1. Composition comprising flocoumafen, wherein;
said composition comprising flocoumafen either includes:
  a non-zero amount of a configurational stereoisomer of flocoumafen, named enantiomer $E_4$, said enantiomer $E_4$ being one of the configurational stereoisomers of one of the two diastereoisomers, said diastereoisomer $D_{1,4}$, of flocoumafen, such that the ratio of this amount to the amount of flocoumafen in the composition is less than 10%, said enantiomer $E_4$ having, by chromatographic analysis of a flocoumafen composition comprising four configurational stereoisomers of flocoumafen, a retention time $t_4$ having a value such that $t_1 < t_2 < t_3 < t_4$; $t_1$, $t_2$ and $t_3$ representing the retention times of the configurational stereoisomers of flocoumafen different from said enantiomer $E_4$; wherein the amount of said enantiomer $E_4$ in the composition is different from the amount of a configurational stereoisomer of flocoumafen, named enantiomer $E_1$, said enantiomer $E_1$ being the other configurational stereoisomer of said diastereoisomer $D_{1,4}$, different from said enantiomer $E_4$ and having, by chromatographic analysis of a flocoumafen composition under the conditions mentioned below, a retention time $t_1$ having a value such that $t_1 < t_2 < t_3 < t_4$, or;
  alternatively said composition comprising flocoumafen comprises a non-zero amount of a configurational stereoisomer of flocoumafen, named enantiomer $E_1$, said enantiomer $E_1$ having, by chromatographic analysis of a flocoumafen composition comprising four configurational stereoisomers of flocoumafen, under the conditions mentioned below, a retention time $t_1$ having a value such that $t_1 < t_2 < t_3 < t_4$, said enantiomer $E_1$ being one of the configurational stereoisomers of one of the two diastereoisomers, said diastereoisomer $D_{1,4}$ of flocoumafen, said enantiomer $E_1$ being different from a configurational stereoisomer of flocoumafen, named enantiomer $E_4$, said enantiomer $E_4$ being the other configurational stereoisomer of said diastereoisomer $D_{1,4}$ said enantiomer $E_4$ having, by chromatographic analysis of a flocoumafen composition comprising four configurational stereoisomers of flocoumafen, a retention time $t_4$ having a value such that $t_1 < t_2 < t_3 < t_4$, said composition comprising flocoumafen being free of said enantiomer $E_4$;
the chromatographic analysis being performed at a temperature of 23.5° C. and under the conditions below:
on a high-pressure liquid chromatography column of dimensions 150×2 mm, and comprising a chiral stationary phase constituted of particles of tris(4-chloro-3-methylphenyl carbamate) cellulose, said particles having a mean size of 3 µm and having a mean pore size of 1000 Å;
using, as liquid mobile phase, a mixture formed from acetonitrile (A) and water comprising 0.1% by volume of formic acid (B), with an AB volume ratio of 92/8 and with a flow rate of the liquid mobile phase in the chromatography column of 0.25 mL/minute;
by injection into the chromatography column of a volume of 1 µL of flocoumafen composition at a concentration of 1 µg of flocoumafen per millilitre of acetonitrile.

2. Composition according to claim 1, comprising an amount of a configurational stereoisomer of flocoumafen, named enantiomer $E_2$, which has, by chromatographic analysis of a flocoumafen composition comprising four configurational stereoisomers of flocoumafen performed under the abovementioned conditions, a retention time $t_2$ having a value such that $t_1 < t_2 < t_3 < t_4$, the amount of said enantiomer $E_2$ being such that the ratio of this amount to the amount of flocoumafen in the composition is less than 10%.

3. Composition according to claim 1, comprising an amount of a configurational stereoisomer of flocoumafen, named enantiomer $E_3$, which has, by chromatographic analysis of a flocoumafen composition comprising four configurational stereoisomers of flocoumafen performed under the abovementioned conditions, a retention time $t_3$ having a value such that $t_1 < t_2 < t_3 < t_4$, the amount of said enantiomer $E_3$ being such that the ratio of this amount to the amount of flocoumafen in the composition is less than 10%.

4. Composition according to claim 1, comprising an amount of a configurational stereoisomer of flocoumafen, named enantiomer $E_1$, which has, by chromatographic analysis of a flocoumafen composition comprising four configurational stereoisomers of flocoumafen performed under the abovementioned conditions, a retention time $t_1$ having a value such that $t_1 < t_2 < t_3 < t_4$, the ratio of the amount of said enantiomer $E_1$ in the composition to the amount of flocoumafen in the composition being between 30% and 100%.

5. Rodenticidal bait comprising a composition according to claim 1 and at least one excipient that is edible for target rodent pests.

6. Bait according to claim 5, wherein the edible excipient comprises at least one food chosen from the group formed from cereal seeds, cereal seed meals, cereal seed flours, cereal seed flakes, cereal bran and non-cereal seeds.

7. Bait according to claim 5, comprising a mass amount of flocoumafen such that the ratio of this mass amount of flocoumafen to the mass amount of rodenticidal bait is less than 200 ppm.

8. Process for controlling target rodent pests, in which there is spread an amount of rodenticidal bait comprising flocoumafen, said bait comprising:
at least one excipient that is edible for target rodent pests, wherein the rodenticidal bait comprises either;
  a non zero amount of a configurational stereoisomer of flocoumafen, named enantiomer $E_4$, said enantiomer $E_4$ being one of the configurational stereoisomers of one of the two diastereoisomers, said diastereoisomer $D_{1,4}$, of flocoumafen, such that the ratio of this amount to the amount of flocoumafen in the composition is less than 10%, said enantiomer $E_4$ having, by chromatographic analysis of a flocoumafen composition comprising four configurational stereoisomers of flocoumafen, a retention time $t_4$ having a value such that $t_1 < t_2 < t_3 < t_4$; $t_1$, $t_2$ and $t_3$ representing the retention times of the configurational stereoisomers of flocoumafen different from said stereoisomer $E_4$; characterized in that wherein the amount of said enantiomer $E_4$ in the composition is different from the amount of a configurational stereoisomer of flocoumafen, named enantiomer $E_1$, said enantiomer $E_1$ being the other configurational stereoisomer of said diasereoisomer $D_{1,4}$, different of said enantiomer $E_4$ and having, by chromatographic analysis of a flocoumafen composition under the abovementioned conditions, a retention time $t_1$ having a value such that $t_1<t_2<t_3<t_4$, or;

alternatively the rodenticidal bait comprises (may comprise) a non-zero amount of a configurational stereoisomer of flocoumafen, named enantiomer $E_1$, said enantiomer $E_1$ having, by chromatographic analysis of a flocoumafen composition comprising four configurational stereoisomers of flocoumafen, under the conditions mentioned below, a retention time $t_1$ having a value such that $t_1<t_2<t_3<t_4$, said enantiomer $E_1$ being one of the configurational stereoisomers of one of the two diastereoisomers, said diastereoisomer $D_{1,4}$ of flocoumafen, said enantiomer $E_1$ being different from a configurational stereoisomer of flocoumafen, named enantiomer $E_4$, said enantiomer $E_4$ being the other configurational stereoisomer of said diastereoisomer $D_{1,4}$ said enantiomer $E_4$ having, by chromatographic analysis of a flocoumafen composition comprising four configurational stereoisomers of flocoumafen, a retention time $t_4$ having a value such that $t_1<t_2<t_3<t_4$, said composition comprising flocoumafen being free of said enantiomer $E_4$;

the chromatographic analysis being performed at a temperature of 23.5° C. and under the conditions below:

on a high-pressure liquid chromatography column of dimensions 150×2 mm, and comprising a chiral stationary phase constituted of particles of tris(4-chloro-3-methylphenyl carbamate) cellulose, said particles having a mean size of 3 μm and having a mean pore size of 1000 Å;

using, as liquid mobile phase, a mixture formed from acetonitrile (A) and water comprising 0.1% by volume of formic acid (B), with an AB volume ratio of 92/8 and with a flow rate of the liquid mobile phase in the chromatography column of 0.25 mL/minute;

by injection into the chromatography column of a volume of 1 μL of flocoumafen composition at a concentration of 1 μg of flocoumafen per millilitre of acetonitrile.

9. Process according to claim 8, wherein the following are chosen in combination:

the edible excipient;

an amount of said enantiomer $E_4$ relative to the flocoumafen;

a mass proportion of flocoumafen in the rodenticidal bait; and an amount of spread rodenticidal bait;

so that target rodent pests consume an amount of flocoumafen that is sufficient to be lethal to said target rodent pests which consume said rodenticidal bait in the course of a single period of 24 consecutive hours.

10. Process according to claim 8, wherein the following are chosen in combination:

the edible excipient;

an amount of said enantiomer $E_4$ relative to the flocoumafen;

a mass proportion of flocoumafen in the rodenticidal bait; and an amount of spread rodenticidal bait;

so that target rodent pests consume an amount of flocoumafen:

which is non-lethal for target rodent pests which consume said rodenticidal bait over a single period of 24 consecutive hours; and which is sufficient to be lethal to target rodent pests which consume said rodenticidal bait over several 24-hour periods, said periods being consecutive.

11. Chromatographic process for separating the configurational stereoisomers of flocoumafen, in which:

a high-pressure liquid chromatography column of dimensions 150×2 mm, and comprising a chiral stationary phase constituted of particles of tris(4-chloro-3-methylphenyl carbamate) cellulose, is chosen, said particles having a mean size of 3 μm and having a mean pore size of 1000 Å;

a mixture formed from acetonitrile (A) and water comprising 0.1% by volume of formic acid (B), with an AB volume ratio of 92/8 and with a flow rate of the liquid mobile phase in the chromatography column of 0.25 mL/minute, is chosen as liquid mobile phase;

separation of the configurational stereoisomers is performed at room temperature, during which:

a liquid composition comprising configurational stereoisomers of flocoumafen is introduced into the top of the chromatography column; and then the liquid composition is entrained with the mobile phase in the chromatography column under conditions suitable for separating the configurational stereoisomers of flocoumafen, and a plurality of fractions of the mobile phase are collected, each fraction comprising one of the configurational stereoisomers of flocoumafen separately from the other configurational stereoisomers of flocoumafen; and the liquid mobile phase of each fraction is removed so as to obtain each configurational stereoisomer.

12. Composition according to claim 2, comprising an amount of a configurational stereoisomer of flocoumafen, named enantiomer $E_3$, which has, by chromatographic analysis of a flocoumafen composition comprising four configurational stereoisomers of flocoumafen performed under the abovementioned conditions, a retention time $t_3$ having a value such that $t_1<t_2<t_3<t_4$, the amount of said enantiomer $E_3$ being such that the ratio of this amount to the amount of flocoumafen in the composition is less than 10%.

13. Composition according to claim 1, comprising an amount of a configurational stereoisomer of flocoumafen, named enantiomer $E_1$, which has, by chromatographic analysis of a flocoumafen composition comprising four configurational stereoisomers of flocoumafen performed under the abovementioned conditions, a retention time $t_1$ having a value such that $t_1<t_2<t_3<t_4$, the ratio of the amount of said enantiomer $E_1$ in the composition to the amount of flocoumafen in the composition being between 30% and 100%.

14. Composition according to claim 2, comprising an amount of a configurational stereoisomer of flocoumafen, named enantiomer $E_1$, which has, by chromatographic analysis of a flocoumafen composition comprising four configurational stereoisomers of flocoumafen performed under the abovementioned conditions, a retention time $t_1$ having a value such that $t_1<t_2<t_3<t_4$, the ratio of the amount of said enantiomer $E_1$ in the composition to the amount of flocoumafen in the composition being between 30% and 100%.

15. Composition according to claim 3, comprising an amount of a configurational stereoisomer of flocoumafen, named enantiomer $E_1$, which has, by chromatographic analysis of a flocoumafen composition comprising four configurational stereoisomers of flocoumafen performed under the abovementioned conditions, a retention time $t_1$ having a value such that $t_1<t_2<t_3<t_4$, the ratio of the amount of said enantiomer $E_1$ in the composition to the amount of flocoumafen in the composition being between 30% and 100%.

16. Rodenticidal bait comprising a composition according to claim 2 and at least one excipient that is edible for target rodent pests.

* * * * *